(12) United States Patent
Patangay et al.

(10) Patent No.: US 8,972,008 B2
(45) Date of Patent: *Mar. 3, 2015

(54) SYSTEM AND METHOD FOR SYSTOLIC INTERVAL ANALYSIS

(71) Applicant: Cardiac Pacemakers, Inc., St. Paul, MN (US)

(72) Inventors: Abhilash Patangay, Inver Grove Heights, MN (US); Krzysztof Z. Siejko, Maple Grove, MN (US); Gerrard M. Carlson, Houston, TX (US); Loell Boyce Moon, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 36 days.

This patent is subject to a terminal disclaimer.

(21) Appl. No.: 13/750,458

(22) Filed: Jan. 25, 2013

(65) Prior Publication Data

US 2013/0138008 A1    May 30, 2013

Related U.S. Application Data

(63) Continuation of application No. 11/553,179, filed on Oct. 26, 2006, now Pat. No. 8,364,263.

(51) Int. Cl.
*A61N 1/00* (2006.01)
*A61B 5/0265* (2006.01)
(Continued)

(52) U.S. Cl.
CPC ............. *A61B 5/0265* (2013.01); *A61B 5/0456* (2013.01); *A61B 5/053* (2013.01); *A61B 5/0538* (2013.01); *A61B 7/04* (2013.01); *A61N 1/36521* (2013.01); *A61N 1/36578* (2013.01);
(Continued)

(58) Field of Classification Search
CPC . A61N 1/362; A61N 1/3627; A61N 1/36521; A61N 1/36578; A61N 1/36585; A61N 1/36571
USPC .................................. 600/528, 514; 607/4–28
See application file for complete search history.

(56) References Cited

U.S. PATENT DOCUMENTS

| 5,334,222 A | 8/1994 | Salo et al. |
| 5,554,177 A | 9/1996 | Kieval et al. |

(Continued)

FOREIGN PATENT DOCUMENTS

| WO | WO-0243587 A1 | 6/2002 |
| WO | WO-2005107582 A1 | 11/2005 |

(Continued)

OTHER PUBLICATIONS

"U.S. Appl. No. 11/553,179, Notice of Allowance mailed Sep. 24, 2012", 5 pgs.

(Continued)

*Primary Examiner* — Scott Getzow
(74) *Attorney, Agent, or Firm* — Schwegman Lundberg & Woessner, P.A.

(57) ABSTRACT

A system and method provide for systolic interval analysis. In an example, an implantable device measures a cardiac impedance signal. A transformation of the cardiac impedance interval is generated. The device also measures a heart sound signal. A time interval between a point on the transformed signal of the cardiac impedance signal and a point on the heart sound signal is calculated.

20 Claims, 4 Drawing Sheets

(51) Int. Cl.
*A61B 5/0456* (2006.01)
*A61B 5/053* (2006.01)
*A61B 7/04* (2006.01)
*A61N 1/365* (2006.01)
*A61B 5/029* (2006.01)
*A61B 5/00* (2006.01)
*A61B 7/00* (2006.01)
*A61B 5/042* (2006.01)

(52) U.S. Cl.
CPC ............ *A61N1/36585* (2013.01); *A61B 5/029* (2013.01); *A61B 5/4836* (2013.01); *A61B 5/686* (2013.01); *A61B 5/7282* (2013.01); *A61B 7/00* (2013.01); *A61N 1/36571* (2013.01); *A61B 5/7239* (2013.01); *A61B 5/0031* (2013.01); *A61B 5/042* (2013.01)
USPC .......................................... 607/18; 600/514

(56) References Cited

U.S. PATENT DOCUMENTS

| | | | |
|---|---|---|---|
| 5,674,256 | A | 10/1997 | Carlson |
| 5,792,195 | A | 8/1998 | Carlson et al. |
| 5,836,987 | A | 11/1998 | Baumann et al. |
| 6,026,324 | A | 2/2000 | Carlson |
| 6,449,509 | B1 | 9/2002 | Park |
| 6,643,548 | B1 | 11/2003 | Mai et al. |
| 7,113,825 | B2 | 9/2006 | Pastore et al. |
| 7,115,096 | B2 | 10/2006 | Siejko et al. |
| 7,123,962 | B2 | 10/2006 | Siejko et al. |
| 7,431,699 | B2 | 10/2008 | Siejko et al. |
| 7,689,283 | B1 | 3/2010 | Schecter |
| 7,736,319 | B2 | 6/2010 | Patangay et al. |
| 2004/0102712 | A1 | 5/2004 | Belalcazar et al. |
| 2006/0224188 | A1 | 10/2006 | Libbus et al. |
| 2007/0093872 | A1 | 4/2007 | Chirife et al. |
| 2008/0103399 | A1 | 5/2008 | Patangay et al. |
| 2012/0296228 | A1 | 11/2012 | Zhang et al. |
| 2013/0030484 | A1 | 1/2013 | Zhang et al. |
| 2013/0053716 | A1 | 2/2013 | Zhang et al. |
| 2014/0207206 | A1 | 7/2014 | Patangay et al. |

FOREIGN PATENT DOCUMENTS

| | | |
|---|---|---|
| WO | WO-2005110535 A1 | 11/2005 |
| WO | WO-2005123180 A1 | 12/2005 |

OTHER PUBLICATIONS

"U.S. Appl. No. 11/553,179, Notice of Allowance mailed Dec. 14, 2009", 4 pgs.

"U.S. Appl. No. 11/553,179, Office Action mailed Apr. 27, 2009", 4 pgs.

"U.S. Appl. No. 11/553,179, Response filed Jul. 27, 2009 to Non Final Office Action mailed Apr. 27, 2009", 10 pgs.

Kim, D-W., "Detection of Physiological Events by Impedance", Yonsei Medical Journal, 30(1), (1989), 1-11.

Packer, M., et al., "Utility of Impedance Cardiography for the Identification of Short-Term Risk of Clinical Decompensation in Stable Patients With Chronic Heart Failure", Journal of the American College of Cardiology, 47(11), (2006), 2245-2252.

Schecter, Stuart O, "U.S. Appl. No. 11/280,715, filed Nov. 15, 2005", 85 pgs.

Schecter, Stuart O, "U.S. Appl. No. 60/627,889, filed Nov. 15, 2004", 23 pgs.

Schecter, Stuart O, "U.S. Appl. No. 60/634,165, filed 23/08/2004", 50 pgs.

Zhang, Xusheng, et al., "Presentation Abstract—PO02-23—Device-based SubQ Heart Sounds for CRT Timing Optimization", Heart Rhythm 2013; Poster Session II; Thursday, May 9, 2013 9:30am-12:00 PM, (Accessed Jul. 30, 2013), 1 pg.

US 7,706,880, 4/2010, Patangay et al. (withdrawn).

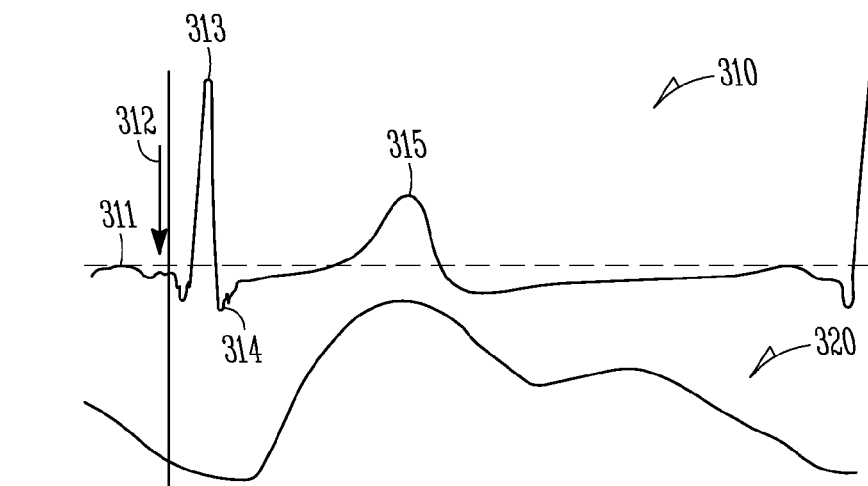
FIG. 3A
FIG. 3B
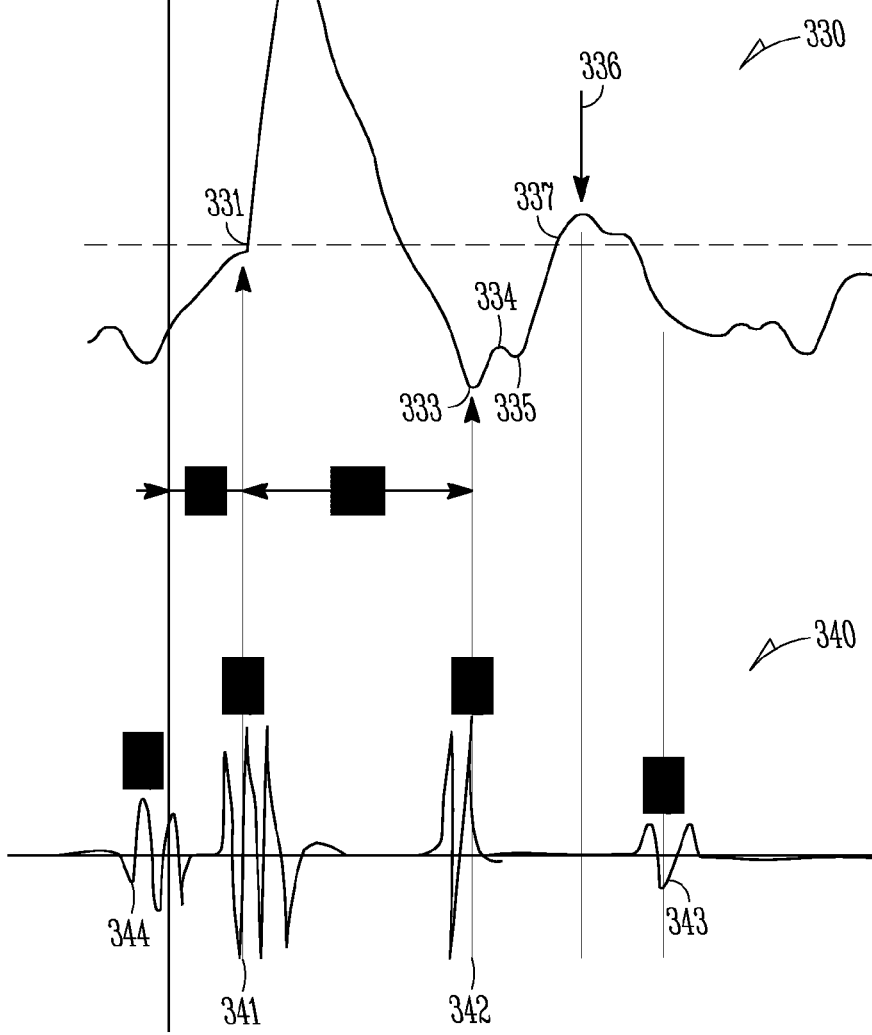
FIG. 3C
FIG. 3D

US 8,972,008 B2

SYSTEM AND METHOD FOR SYSTOLIC INTERVAL ANALYSIS

CLAIM OF PRIORITY

This application is a continuation of and claims the benefit of priority under 35 U.S.C. §120 to Patangay, U.S. patent application Ser. No. 11/553,179, entitled "System and Method for Systolic interval Analysis," filed on Oct. 26, 2003, now issued as U.S. Pat. No. 8,364,263 which is hereby incorporated by reference herein in its entirety.

TECHNICAL FIELD

The present disclosure relates to an implantable medical device system, and in an embodiment, but not by way of limitation, an implantable medical device system and method that analyzes systolic intervals.

BACKGROUND

The heart is at the center of the circulatory system. It includes four chambers—two atria and two ventricles. The right atrium receives deoxygenated blood from the body, pumps it into the right ventricle, and the right ventricle pumps the blood to the lungs to be re-oxygenated. The re-oxygenated blood returns to the left atrium, it is pumped into the left ventricle, and then the blood is pumped by the left ventricle throughout the body to meet the hemodynamic needs of the body.

The heart includes a sino-atrial node that generates a depolarization wave that propagates through the heart. The depolarization wave can be sensed in the heart or at the surface of the body. The depolarization wave of a full cardiac cycle includes a P wave, a QRS complex, and a T wave. The P wave represents the atrial depolarization before the atrial contraction, and the QRS complex represents the ventricular depolarization before the ventricular contraction. The T wave represents the ventricular repolarization as the ventricles recover from the depolarization.

Heart sounds are associated with mechanical vibrations from activity of a patient's heart and the flow of blood through the heart. Heart sounds recur with each cardiac cycle and are separated and classified according to the activity associated with the vibration. The first heart sound (S1) is associated with the vibrational sound made by the heart during tensing of the mitral valve. The second heart sound (S2) marks the beginning of diastole. The third heart sound (S3) and fourth heart sound (S4) are related to filling pressures of the left ventricle during diastole. Heart sounds are useful indications of proper or improper functioning of a patient's heart.

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical therapy or to aid a physician or caregiver in patient diagnosis through internal monitoring of a patient's condition. The devices may include electrodes in communication with sense amplifiers to monitor electrical heart activity within a patient, and often include sensors to monitor other internal patient parameters. Other examples of implantable medical devices include implantable diagnostic devices, implantable insulin pumps, devices implanted to administer drugs to a patient, or implantable devices with neural stimulation capability.

Overview

An implantable medical device can be used to detect cardiac impedance signals and heart sound signals. The device can calculate a time interval between a point on the heart sound signal and a point on the cardiac impedance signal. The time interval can be compared to independently specifiable thresholds, such as to trigger an alert or responsive therapy, or to display one or more trends. The time interval information can also be combined with detection of one or more other congestive heart failure (CHF) symptoms to generate a CHF status indicator or to trigger an alarm or responsive therapy or to display one or more trends. The alert can notify a patient or a caregiver, such as via remote monitoring.

In Example 1, a system includes an implantable medical device. The implantable medical device includes a timing circuit, a cardiac impedance sensing circuit that is coupled to the timing circuit and that is configured to detect a cardiac impedance signal, an acoustic sensor that is coupled to the timing circuit and that is configured to sense an acoustic signal, and a heart sound detector circuit that is coupled to the timing circuit and that is configured to detect a heart sound signal in the acoustic signal. The timing circuit is configured to calculate a time interval between a point on the heart sound signal and a point on the cardiac impedance signal.

In Example 2, the system of Example 1 optionally includes a telemetry circuit that is coupled to the timing circuit and that is configured to transmit one or more of heart sound data and cardiac impedance data to one or more of an external device and an external database.

In Example 3, the systems of Examples 1-2 optionally include a transform circuit that is coupled to the timing circuit and that is configured to calculate a transformed signal of the cardiac impedance signal. In Example 3, the timing circuit is optionally configured to calculate a time interval between a point on the heart sound signal and a point on the transformed signal.

In Example 4, the timing circuits of Examples 1-3 are optionally configured to calculate a time interval between a point on the heart sound signal and a point on the transformed signal that calculates a left ventricular ejection time. In Example 4, in the calculation of the left ventricular ejection time the timing circuit optionally uses a point on the heart sound signal indicative of an S1 heart sound, and a point on the transformed signal indicative of an aortic valve closure within a cardiac cycle.

In Example 5, the timing circuits of Examples 1-4 are optionally configured to calculate a time interval between a point on the heart sound signal and a point on the transformed signal that calculates an estimate of pre-ejection time. In Example 5, in the calculation of the estimate of the pre-ejection time, the timing circuit optionally uses a point on the heart sound signal indicative of an S4 heart sound, and a point on the transformed signal indicative of an aortic valve opening within a cardiac cycle.

In Example 6, the timing circuits of Examples 1-5 are optionally configured to calculate the time interval between a point on the heart sound signal indicative of an S4 heart sound, and a point on the transformed signal indicative of a maximum systolic blood flow within a cardiac cycle.

In Example 7, the timing circuits of Examples 1-6 are optionally configured to calculate the time interval between a point on the heart sound signal indicative of an S2 heart sound; and a point on the transformed signal indicative of one of a maximum systolic blood flow within a cardiac cycle, an aortic valve opening within a cardiac cycle, a pulmonary valve closure within a cardiac cycle, an aortic valve closure within a cardiac cycle, or a mitral valve opening within a cardiac cycle.

In Example 8, the timing circuits of Examples 1-7 are optionally configured to calculate the time interval between a point on the heart sound signal indicative of an S1 heart sound; and a point on the transformed signal indicative of one of an aortic valve opening within a cardiac cycle, a pulmonary valve closure within a cardiac cycle, or a mitral valve opening within a cardiac cycle.

In Example 9, the timing circuits of Examples 1-8 are optionally configured to calculate the time interval between a point on the heart sound signal indicative of an S3 heart sound; and a point on the transformed signal indicative of one of an aortic valve closure within a cardiac cycle, a pulmonary valve closure within a cardiac cycle, or a mitral valve opening within a cardiac cycle.

In Example 10, the timing circuits of Examples 1-9 are optionally configured to calculate the time interval over multiple cardiac cycles, and to identify or characterize a decompensation as a function of one or more changes in the time interval over the multiple cardiac cycles.

In Example 11, the systems of Examples 1-10 optionally include an external device. The implantable medical device optionally includes a cardiac sensing circuit that is coupled to the timing circuit and that is configured to detect a cardiac signal; an ensemble averaging circuit that is coupled to the timing circuit and that is configured to generate an ensemble average for one or more of the cardiac signal, the cardiac impedance signal, the heart sound signal, and the transformed signal; and a telemetry circuit. The cardiac signal can be a cardiac electric signal (EGM). The external device optionally includes a telemetry circuit; a memory circuit configured to store one or more of the ensemble averaged cardiac signal, the ensemble averaged cardiac impedance signal, the ensemble averaged heart sound signal, and the ensemble averaged transformed signal; and a timing circuit configured to calculate a second time interval between one or more of (1) a point on the ensemble averaged cardiac signal and a point on the ensemble averaged heart sound signal, (2) a first point on the ensemble averaged heart sound signal and a second point on the ensemble averaged heart sound signal, (3) a point on the ensemble averaged impedance signal and a point on the ensemble averaged heart sound signal, and (4) a point on the ensemble averaged heart sound signal and a point on the ensemble averaged transformed signal.

In Example 12, in the system of Example 11, the point of the ensemble averaged cardiac signal optionally includes a portion of an R wave, and the point of the ensemble averaged heart sound signal is optionally indicative of one of an S1, S2, S3, or S4 heart sound.

In Example 13, the external device memory of Examples 11-12 optionally include one or more of cardiac signal data, cardiac impedance data, heart sound data, and transformed signal data from a population of individuals. The external device is optionally configured to use the cardiac signal, cardiac impedance, heart sound, and transformed signal population data in connection with an analysis of an individual's cardiac signal, cardiac impedance, heart sound, and transformed signal data.

In Example 14, the external devices of Examples 11-13 optionally include or are optionally coupled to one or more external sensors. One or more patient thresholds are optionally set as a function of data received from the one or more external sensors.

In Example 15, the external devices of Examples 11-14 optionally include or are optionally coupled to one or more of an external sensor and a database. The external device further optionally includes a circuit configured to compare one or more of the cardiac signal, the cardiac impedance signal, the heart sound signal, the transformed signal, data from the external sensor, and data from the database.

In Example 16, the external sensors of Examples 11-15 optionally include one or more of a body weight sensor and a blood pressure sensor. The database optionally includes one or more of a medication history, a disease history, a hospitalization history, and one or more population statistics.

In Example 17, a process includes measuring a cardiac impedance signal with an implantable medical device, measuring a heart sound signal with the implantable medical device, and calculating a time interval between a point on the cardiac impedance signal a point on the heart sound signal.

In Example 18, the process of Example 17 optionally includes transforming the cardiac impedance signal into a transformed signal, and calculating a time interval between a point on the transformed signal and a point on the heart sound signal. The transforming may include one or more of a differentiation, a filtering, a derivation, and an integration.

In Example 19, in the processes of Examples 17-18, the calculation of the time interval between a point on the transformed signal of the cardiac impedance signal and a point on the heart sound signal optionally calculates a left ventricular ejection time. The calculation of the left ventricular ejection time optionally uses a point on the heart sound signal indicative of an S1 heart sound, and a point on the transformed signal indicative of an aortic valve closure within a cardiac cycle.

In Example 20, in the processes of Examples 17-19, the calculation of a time interval between a point on the transformed signal of the cardiac impedance signal and a point on the heart sound signal optionally estimates a pre-ejection time. The estimation of the pre-ejection time optionally uses a point on the heart sound signal indicative of an S4 heart sound, and a point on the transformed signal indicative of an aortic valve opening within a cardiac cycle.

In Example 21, in the processes of Examples 17-20, the calculation of the time interval optionally uses a point on the heart sound signal indicative of an S4 heart sound, and a point on the transformed signal indicative of a maximum systolic blood flow within a cardiac cycle.

In Example 22, in the processes of Examples 17-21, the calculation of the time interval optionally uses a point on the heart sound signal indicative of an S2 heart sound; and a point on the transformed signal indicative of a maximum systolic blood flow within a cardiac cycle, an aortic valve opening within a cardiac cycle, a pulmonary valve closure within a cardiac cycle, an aortic valve closure within a cardiac cycle, or a mitral valve closure within a cardiac cycle.

In Example 23, in the processes of Examples 17-22, the calculation of the time interval optionally uses a point on the heart sound signal indicative of an S1 heart sound; and a point on the transformed signal indicative of one of an aortic valve opening within a cardiac cycle, a pulmonary valve closure within a cardiac cycle, or a mitral valve opening within a cardiac cycle.

In Example 24, in the processes of Examples 17-23, the calculation of the time interval optionally uses a point on the heart sound signal indicative of an S3 heart sound; and a point on the transformed signal indicative of one of an aortic valve closure within a cardiac cycle, a pulmonary valve closure within a cardiac cycle, or a mitral valve opening within a cardiac cycle.

In Example 25, the processes of Examples 17-24 optionally include calculating the time interval over multiple cardiac cycles, and identifying or characterizing a decompensation as a function of a change in the time interval over the multiple cardiac cycles.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

FIG. 3A illustrates an example of a cardiac signal.

FIG. 3B illustrates an example of a cardiac impedance signal.

FIG. 3C illustrates an example of a first derivative of a cardiac impedance signal.

FIG. 3D illustrates an example of a heart sound signal.

DETAILED DESCRIPTION

In the following detailed description, reference is made to the accompanying drawings which form a part hereof, and in which is shown by way of illustration specific embodiments in which the disclosure may be practiced. These embodiments, which are also referred to as examples, are discussed in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description provides examples, and the scope of the present disclosure is defined by the appended claims and their equivalents.

It should be noted that references to "an", "one", or "various" embodiments in this disclosure are not necessarily to the same embodiment, and such references contemplate more than one embodiment.

Figure 1:
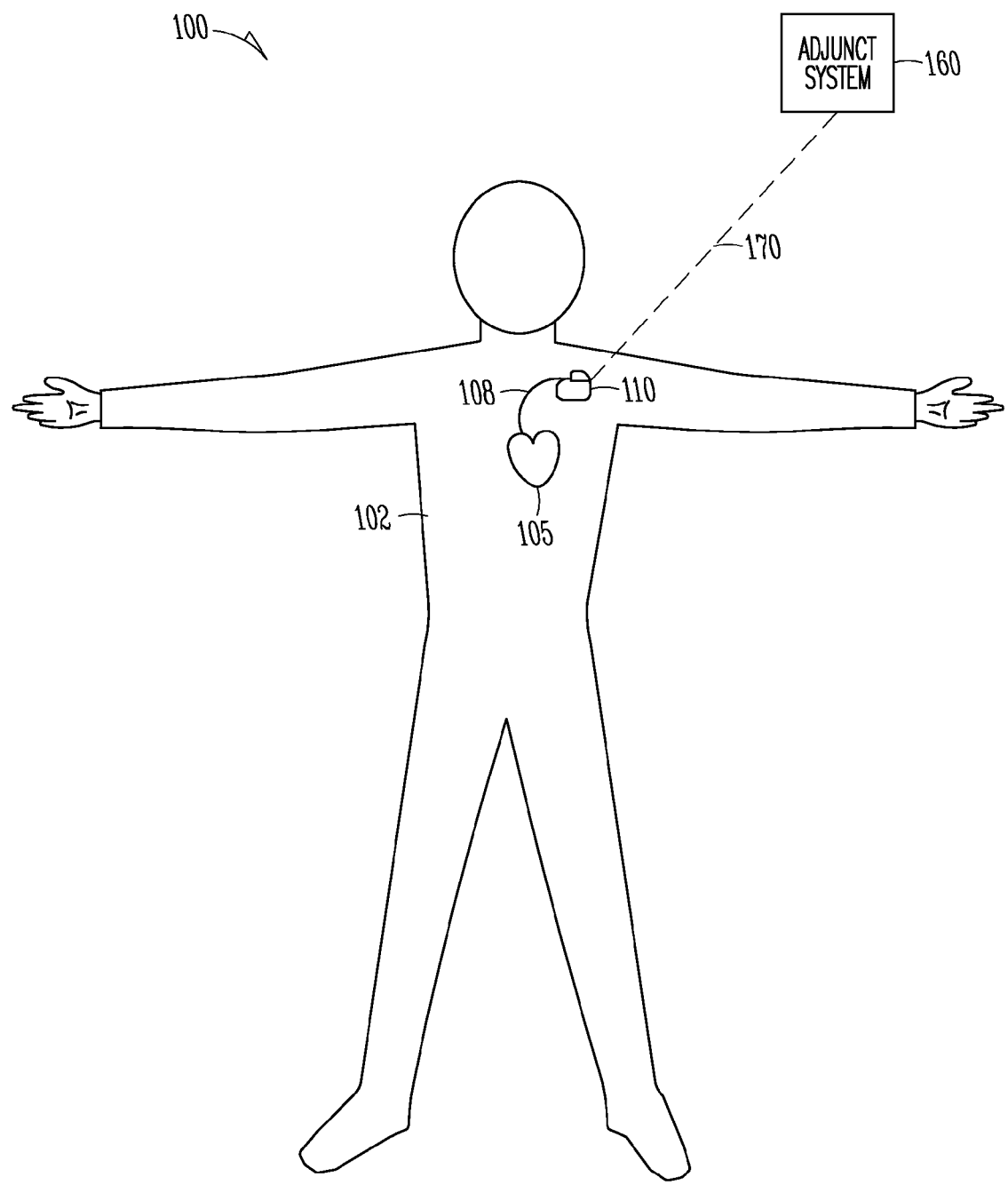
FIG. 1 illustrates an example of an implanted medical device in communication with an adjunct device.
Figure 2:
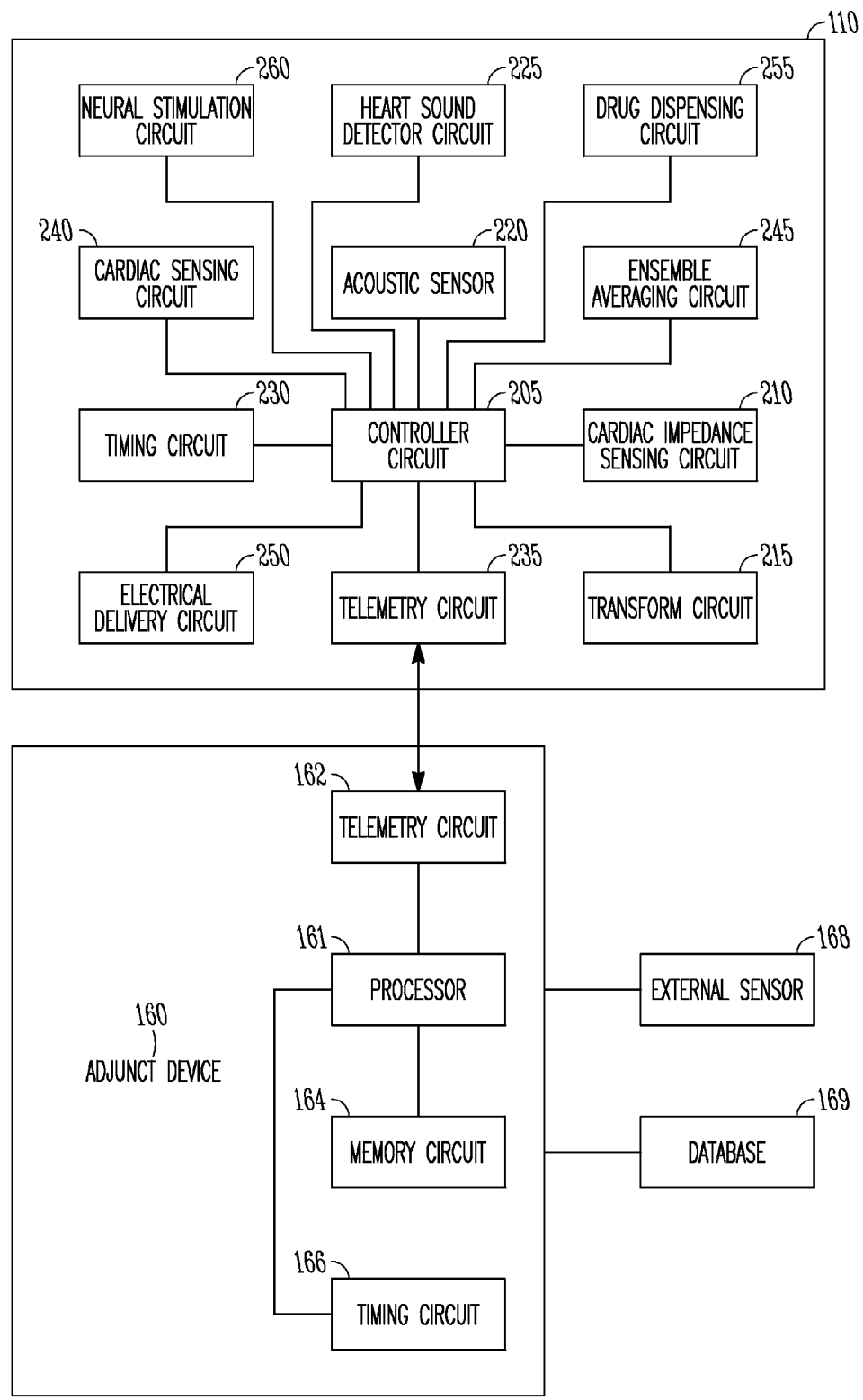
FIG. 2 illustrates an example of an implantable medical device.

FIG. 1 is a diagram illustrating an example of a medical device system 100 that can be used in connection with transmitting data from an implanted device 110 to an adjunct device 160. In an example, the adjunct device 160 is an external device. FIG. 1 illustrates a body 102 with a heart 105. System 100 typically includes the implantable medical device 110, a lead system 108, the adjunct device or system 160, and a wireless telemetry link 170. Data can be transferred from the device 110 to the adjunct system 160 via the telemetry link 170. As illustrated in FIG. 2, the adjunct device 160 may include a processor 161, a telemetry circuit 162, a memory circuit 164, a timing circuit 166, an external sensor 168, and a database 169. The telemetered data may be stored in a memory 164, and may then be used for analysis and interpretation either immediately or at a later time.

FIG. 2 illustrates an example of the implantable medical device 110. The medical device 110 includes a controller circuit 205. A cardiac impedance sensing circuit 210 is connected to the controller circuit 205. In an example, the cardiac impedance sensing circuit 210 is configured to detect a cardiac impedance signal from a heart. The controller circuit 205 is further connected to a transform circuit 215. The transform circuit 215 may be configured to generate, for example, one or more of a derivative waveform, a filtered waveform, or an integrated waveform of a cardiac impedance signal sensed by the cardiac impedance sensing circuit 210. This transformation may be implemented with, for example, a differentiator, a filter (e.g., linear, high pass, low pass, band pass), a derivative circuit, or an integrator circuit. An acoustic sensor 220 is connected to the controller circuit 205. The acoustic sensor 220 may be configured to sense an acoustic signal, and in particular, an acoustic signal generated by a contracting heart. The acoustic sensor 220 may be one or more of several different types of sensors including a microphone, an accelerometer, and a transducer. A heart sound detector circuit 225 is connected to the controller circuit 205. The heart sound detector circuit 225 is primarily configured to detect a heart sound signal in the acoustic signal from the acoustic sensor 220. Also coupled to the controller circuit 205 is a timing circuit 230. The timing circuit 230 is configured to calculate a time interval, such as between a point on a heart sound signal detected by the heart sound detector circuit 225, and a point on the cardiac impedance signal or a point on the transformed signal of the cardiac impedance signal. A telemetry circuit 235 is connected to the control circuit 205. The telemetry circuit 235 can transmit data from the implantable medical device 110 to an adjunct system, such as the adjunct system 160 in FIG. 1. Such transmitted data may include heart sound and other acoustic data, cardiac depolarization data, cardiac impedance data, or transformed signals of the cardiac impedance data. The implantable device 110 may also include an electrical delivery circuit 250, a drug dispensing circuit 255, or a neural stimulation circuit 260.

The implantable medical device 110 may further include a cardiac sensing circuit 240. The cardiac sensing circuit 240 is coupled to the controller circuit 205, and may be configured to detect a cardiac signal generated by a heart. In an example, the implantable medical device 110 may further include an ensemble averaging circuit 245 connected to the controller circuit 205. The ensemble averaging circuit 245 may be configured to generate an ensemble average for any electrical, acoustic, or other signals generated by the body in which the device 110 is implanted, such as cardiac depolarization signals, cardiac impedance signals, heart sound signals, or transformed signals of the cardiac impedance signals. An ensemble average for a buffer of heart sound signal data or other signal data may be generated, such as by a simple summation of the acoustic sensor 220 outputs taken at a specified time relative to a reference point such as a V-event marker. In an example, the ensemble average is of the amplitudes of the heart sound signal.

FIGS. 3A, 3B, 3C, and 3D illustrate examples of a cardiac signal 310, a cardiac impedance signal 320, a first derivative 330 of the cardiac impedance signal 320, and a heart sound signal 340 respectively. The cardiac signal 310 includes a P wave 311, a Q wave 312, an R wave 313, an S wave 314, and a T wave 315. The cardiac impedance signal can include, within a particular cardiac cycle, an absolute maximum, an absolute minimum, local minimums, local maximums, and other identifiable points and slopes (which may correspond to other points of other signals such as a cardiac signal or a first derivative of a cardiac impedance signal). In this example, the first derivative 330 includes a first zero crossing at 331, a cardiac cycle maximum at 332, a cardiac cycle minimum at 333, a local maximum and a local minimum at 334 and 335 respectively, and another local maximum at 336. The heart sound signal 340 includes the S1 heart sound 341, the S2 heart sound 342, the S3 heart sound 343, and the S4 heart sound 344. FIGS. 3A-3D are illustrated such that a point on one of the signal traces at a certain horizontal position represents the same real time as a point on another one of the FIG. 3A, 3B, 3C, or 3D graphs at the same horizontal position. However, while a particular horizontal position on one graph represents the same time as the same horizontal position on another graph, the position of particular features of each graph may change from cardiac cycle to cardiac cycle. For example, the horizontal position of the Q wave 312 may change in relation to the maximum 332 of the first derivative 330. These changes represent time interval changes.

The cardiac impedance signal and the transformed signal of the cardiac impedance signal may also relate to certain identifiable physiological events. For example, in the first derivative of the cardiac impedance signal illustrated in FIG. 3C, 331 is indicative of an aortic valve opening, 332 is indicative of a maximum systolic blood flow, 333 is indicative of an aortic valve closure, 334/335 is indicative of a pulmonary valve closure, and 336 is indicative of a mitral valve opening.

The timing relationship of the signals in FIGS. 3A-3D permit a comparison of the time relationship of any point on one of the signals, e.g., the S4 heart sound signal 344 on the heart sound signal 340, and any point on another signal or transformed signal, e.g., the first zero crossing 331 on the first derivative 330. For example, the timing circuit 230, in conjunction with the heart sound detector circuit 225 and the first derivative circuit 215, may be configured to calculate any time interval between the first derivative 330 and the heart sound signal 340. As another example, timing circuit 230 may calculate the time interval between a point on the cardiac impedance signal 320 and a point on the heart sound signal 340. As yet another example, the timing circuit 230 may calculate the time interval between a point on the heart sound signal 340 and another other signal transformation of the cardiac impedance signal 320.

For example, the timing circuit 230 may be configured to calculate a left ventricular ejection time (LVET) time interval between a point on the heart sound signal 340 and a point on the first derivative 330. The calculation of the LVET uses a point on the heart sound signal representing the S1 heart sound 341, and a point on the first derivative representing an absolute minimum 333 within a particular cardiac cycle. Similarly, an LVET may be calculated using a point on the heart sound signal representing the S1 heart sound 341, and a point on a transformed cardiac impedance signal indicative of an aortic valve closure within a cardiac cycle.

Similarly, the timing circuit 230 may be configured to calculate a time interval between a point on the heart sound signal 340 and a point on the first derivative 330. The calculation of this time interval may use a point on the heart sound signal representing the S4 heart sound 344, and a point on the first derivative representing a first zero crossing 331 within a cardiac cycle. Similarly, the calculation of this time interval may use a point on the heart sound signal representing the S4 heart sound 344, and a point on a transformed cardiac impedance signal indicative of an aortic valve opening within a cardiac cycle.

Any time interval between any two points on one or more of the cardiac signal 310, the cardiac impedance signal 320, the first derivative signal 330, the heart sound signal 340, and a transformed cardiac impedance signal may be calculated. For example, the timing circuit 230 may be configured to calculate a time interval between a point on the heart sound signal 340 representing an S4 heart sound 344, and a point on the first derivative representing an absolute maximum 332 within a particular cardiac cycle. The timing circuit 230 may also be configured to calculate a time interval between a point on the heart sound signal 340 representing an S4 heart sound 344, and a point on a transformed cardiac impedance signal indicative of an aortic valve opening within a cardiac cycle. As another example, the timing circuit 230 may be configured to calculate a time interval between a point on the heart sound signal 340 representing an S2 heart sound 342, and any one of the following points on the first derivative signal 330—an absolute maximum 332 within a cardiac cycle, a first zero crossing 331 within a cardiac cycle, a local maximum 334 or a local minimum 335 after an absolute minimum 333 within a cardiac cycle, an absolute minimum 333 within a cardiac cycle, or a local maximum 336 above a zero crossing 337 after an absolute minimum 333 within a cardiac cycle. The timing circuit 230 may also be configured to calculate a time interval between a point on the heart sound signal 340 representing an S2 heart sound 342, and any one of the following points on another transformed signal of a cardiac impedance signal—a point indicative of a maximum systolic blood flow within a cardiac cycle, an aortic valve opening within a cardiac cycle, a pulmonary valve closure within a cardiac cycle, an aortic valve closure within a cardiac cycle, or mitral valve opening within a cardiac cycle. Also, as another example, the timing circuit 230 may be configured to calculate the time interval between a point on the heart sound signal 340 representing an S1 heart sound 341, and any one of the following points on the first derivative signal 330—a first zero crossing 331 within a cardiac cycle, a local minimum 335 or a local maximum 334 after an absolute minimum 333 within a cardiac cycle, or a local maximum 336 above a zero crossing 337 after an absolute minimum 333 within a cardiac cycle. The timing circuit 230 may also be configured to calculate the time interval between a point on the heart sound signal 340 representing an S1 heart sound 341, and any one of the following points on a transformed cardiac impedance signal—a point indicative of an aortic valve opening within a cardiac cycle, a pulmonary valve closure within a cardiac cycle, or a mitral valve opening within a cardiac cycle. As yet another example, the timing circuit 230 may be configured to calculate a time interval between a point on the heart sound signal 340 representing an S3 heart sound 343, and any one of the following points on the first derivative signal 330—an absolute minimum 333 within a cardiac cycle, a local maximum 334 or a local minimum 335 after an absolute minimum 333 within a cardiac cycle, or a local maximum 336 above a zero crossing 337 after an absolute minimum 333 within a cardiac cycle. The timing circuit 230 may be configured to calculate a time interval between a point on the heart sound signal 340 representing an S3 heart sound 343, and any one of the following points on a transformed cardiac impedance signal—a point representing an aortic valve closure within a cardiac cycle, a pulmonary valve closure within a cardiac cycle, or a mitral valve opening within a cardiac cycle. These are just examples of some of the intervals that may be analyzed between a heart sound signal 340 and a first derivative 330 or other transformed signal of a cardiac impedance signal 320.

The information and data that may be obtained from the calculation of these time intervals may be used for many purposes. For example, the timing circuit 230 may be configured to calculate one or more of these time intervals over multiple cardiac cycles, and further configured to then use the data from these multiple cardiac cycles to identify an episode of heart failure decompensation as a function of one or more changes in the time interval over the multiple cardiac cycles. For example, if the left ventricular ejection time (LVET) is decreasing over multiple cardiac cycles, then this may indicate that the left ventricle is pumping less blood for each systolic contraction, indicating that the patient's heart condition is worsening. As another example, if the pre-ejection period (PEP, or pre-ejection time) is increasing over multiple cardiac cycles, then that may indicate that contraction of the heart is taking longer, thereby taking more time to build up pressure in the heart chambers, which can result in less blood in the left ventricle to be pumped to the body during systole. In this example, PEP may be defined as the interval from the start of electrical left ventricle depolarization to the onset of aortic ejection in early systole. This interval can be approximated by the time difference between a point on the QRS complex (such as the R-wave or a pacing spike) and a point on the transformed impedance cardiogram that corresponds to an onset of aortic flow, such as 331 in FIG. 3C. Similarly, PEP can also be estimated using the heart sounds waveform by using a point in the S1 waveform complex that corresponds to an aortic opening.

A ratio of the LVET and PEP intervals can be used to estimate left ventricle stroke volume and cardiac output. In a patient with progressively worsening heart failure, as alluded to above, the LVET decreases and the PEP increases. Therefore, relative increases in a patient's PEP/LVET ratio can be used to alert health care providers of potentially diminished cardiac output. Furthermore, a calibrated PEP/LVET ratio can be used as an instantaneous estimate of a patient's cardiac output or stroke volume.

As it relates to one or more examples in this disclosure, heart failure deocompensation further includes thoracic fluid accumulation and pulmonary edema. One or more examples in this disclosure can heart failure disease status, progression, and the onset of heart failure decompensation which may lead to hospitalization. However, an early alert to the onset of decompensation by one or more of the examples of this disclosure may lead to therapeutic interventions which may prevent the hospitalization or reduce its duration. An example of a therapeutic intervention may involve an implantable drug delivery system such as drug dispensing circuit 255.

In general, any time interval between any points on one or more of the cardiac signal 310, the cardiac impedance signal 320, the first derivative signal 330, the heart sound signal 340, and a transformation of the cardiac impedance signal 320 may be analyzed over multiple cardiac cycles to determine if that interval is increasing or decreasing over time. A study may be performed among a population to determine the relationship between any particular time interval and the progression or regression of the patient's heart condition. After such a relationship is identified, then that relationship may be applied to other individuals, such as to identify a progression or regression of an individual patient's heart condition based on that particular time interval.

In certain examples, more complex analyses of heart sound data and cardiac depolarization data may be implemented, such as where the implantable device 110 includes a cardiac sensing circuit 240, an ensemble averaging circuit 245, and a telemetry circuit 235, and further where an adjunct or external system 160 includes a memory circuit 164 and a timing circuit 166. For example, an ensemble average may be calculated for a plurality of cardiac signals and a plurality of heart sound signals. The calculation of an ensemble average, among other things, performs signal conditioning by removing noise from the cardiac and heart sound signals, and can further perform compression.

The timing circuit 166 of the external device 160 may be configured to calculate a time interval between a point on the ensemble averaged cardiac depolarization signal and a point on the ensemble averaged heart sound signal. The timing circuit 166 could further be configured to calculate a time interval between a first point on the ensemble averaged heart sound signal and a second point on the ensemble averaged heart sound signal. For example, the point on the ensemble averaged cardiac signal may represent a portion of an R wave, and the point on the ensemble averaged heart sound signal may represent a portion of one of an S1, S2, S3, or S4 heart sound. For example, the first point on the ensemble averaged heart sound signal may represent an S1 heart sound and the second point on the ensemble averaged heart sound signal may represent an S2 heart sound.

The memory 164 in the external device 160 and/or the database 169 may include a patient medication history, a disease history, a hospitalization history, and/or population statistics. The processor 161 of the external device may then be configured to use this data in analyzing an individual's data. The processor 161 may further be configured to compute a trend in any time interval relating to this data. The external device 160 may further be communicatively coupled to one or more external sensors 168. These external sensors may collect physiological data from the patient (e.g., blood pressure). The external device may then set one or more patient thresholds as a function of data received from the one or more external sensors.

Based on the data and/or trend in the cardiac and heart sound data, the external device 160 may transmit a signal to the implantable device 110. This signal can be used to modify the therapy of the device 110. The signal can alter the pacing of the electrical delivery circuit 250, alter the level of a pharmaceutical dispensed by the drug dispensing circuit 255, and/or alter the level of stimulation by the neural stimulation circuit 260. The electrical delivery circuit 250 may alter pacing pulses delivered to a heart, such as by altering the pacing rate, the pulse width, the pulse amplitude, and other features. The location of the heart to which the pulse is delivered may also be altered. Similarly, the AV delay or other interelectrode delay of the pulses may be altered. As these therapies are altered, the device 110 may then collect additional cardiac and heart sound data, this data may be telemetered to the external device 160, and the external device may re-calculate the cardiac and heart sound intervals to determine the effect that the change in therapy had on those intervals.

Figure 4:
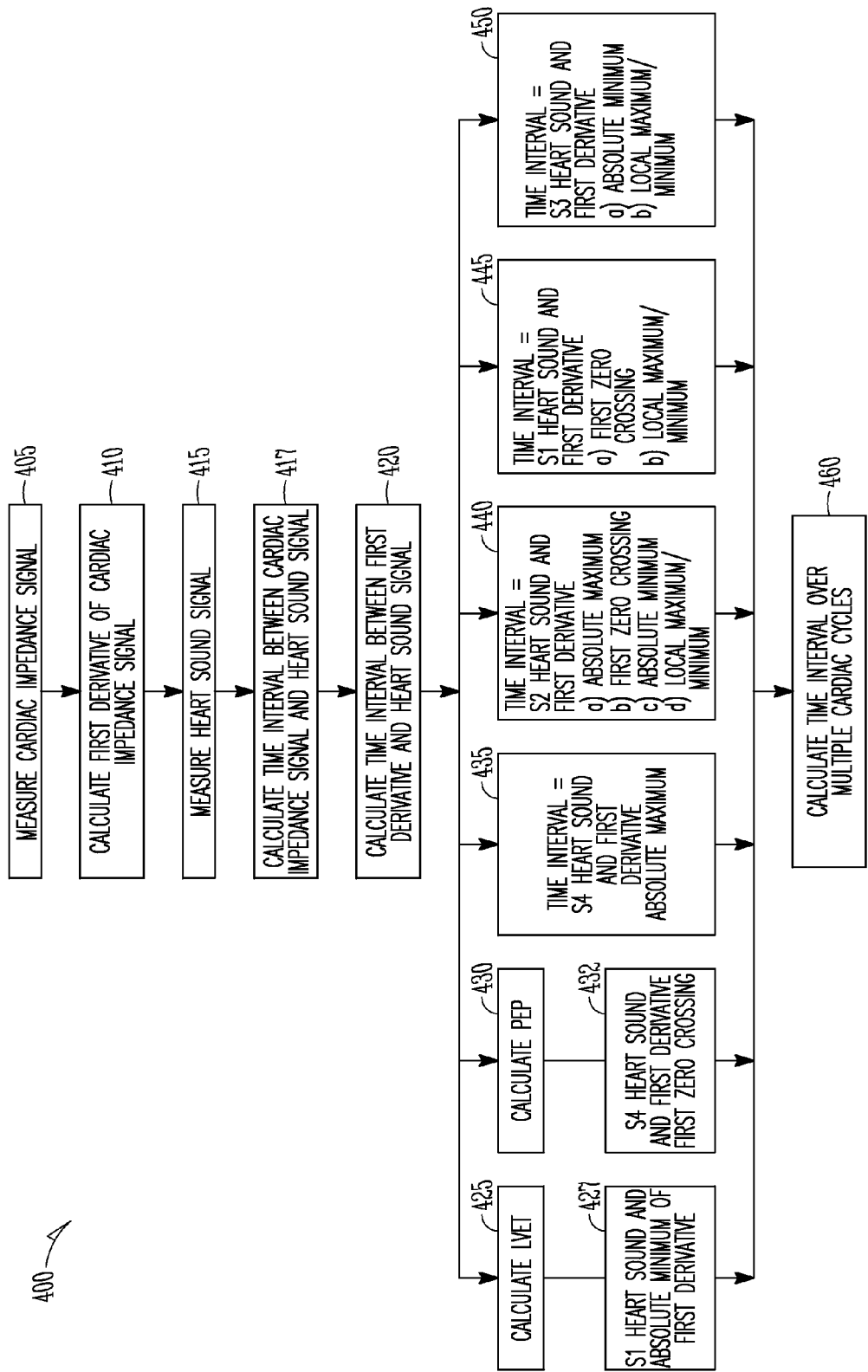
FIG. 4 illustrates an example of a process to calculate systolic time intervals.

FIG. 4 illustrates an example of a process 400 that calculates a time interval between a point on a cardiac impedance signal and a heart sound signal, and a point on a first derivative of a cardiac impedance signal and a point on a heart sound signal. In other examples, functions of these signals can be used such as multiple derivatives, filtered signals, and other transformations of a cardiac impedance signal. At 405, a cardiac impedance signal is measured. At 410, a first derivative of that cardiac impedance signal is calculated. At 415, a heart sound signal is measured. At 417, the time interval between a point on a cardiac impedance signal and a point on a heart sound signal is calculated, and at 420, the time interval between a point on the first derivative of the cardiac impedance signal and a point on the heart sound signal is calculated.

As further indicated in FIG. 4, the process 400 may use one of several points on the first derivative signal and one of several points on the heart sound signal. For example, at 425, the calculation of the time interval between a point on the first derivative of the cardiac impedance signal and a point on the heart sound signal may include a left ventricular ejection time. As further indicated at 427, this left ventricular ejection time may be calculated by using a point on the heart sound signal representing an S1 heart sound, and a point on the first derivative representing an absolute minimum within a cardiac cycle. Similarly, as indicated at 430, the process 400 may calculate a time interval between a point on the first derivative of the cardiac impedance signal and a point on the heart sound signal that results in the pre-ejection time. At 432, the pre-ejection time is calculated, such as by using a point on the heart sound signal representing an S4 heart sound, and a point on the first derivative representing a first zero crossing within a cardiac cycle. At 435, the process 400 calculates a time interval, such as by using a point on the heart sound signal representing an S4 heart sound, and a point on the first derivative representing an absolute maximum within a cardiac cycle. At 440, the process 400 calculates a time interval, such as by using a point on the heart sound signal representing an S2 heart sound, and a point on the first derivative representing one of an absolute maximum within a cardiac cycle, a first zero crossing within a cardiac cycle, a local maximum or a local minimum after an absolute minimum within a cardiac cycle, an absolute minimum within a cardiac cycle, or a local maximum above a zero crossing after an absolute minimum within a cardiac cycle. At 445, the process 400 calculates a time interval, such as by using a point on the heart sound signal representing an S1 heart sound, and a point on the first derivative representing one of a first zero crossing within a cardiac cycle, a local minimum or a local maximum after an absolute minimum within a cardiac cycle, or a local maximum above a zero crossing after an absolute minimum within a cardiac cycle. This time may be used to approximate the isovolumic contraction time (IVCT). At 450, the process 400 calculates a time interval, such as by using a point on the heart sound signal representing an S3 heart sound, and a point on the first derivative representing one of an absolute minimum within a cardiac cycle, a local maximum or a local minimum after an absolute minimum within a cardiac cycle, or a local maximum above a zero crossing after an absolute minimum within a cardiac cycle.

At 460, the process 400 calculates a time interval, such as one or more of the above disclosed time intervals, over multiple cardiac cycles, and identifies a decompensation or other condition as a function of a change in the time interval over the multiple cardiac cycles.

In another example process includes the steps of measuring a cardiac impedance signal with an implantable medical device, measuring a cardiac electrical signal with the implantable medical device (the cardiac electrical signal including an R-wave), measuring a heart sound signal with the implantable medical device (the heart sound signal including an S2 heart sound), transforming the cardiac impedance signal into a transformed signal (the transformed signal including a portion indicative of an aortic opening), estimating a pre-ejection time by calculating an interval between the R-wave on the cardiac electrical signal and the aortic opening on the transformed cardiac impedance signal, and estimating a left ventricular ejection time by calculating an interval between the S2 heart sound on the heart sound signal and the aortic opening on the transformed cardiac impedance signal. The process may further include calculating a ratio of the pre-ejection time and the left ventricular ejection time. In this process, the transformation of the cardiac impedance signal can include one or more of differentiation, a filtering, a derivation, and an integration.

In the above detailed description of embodiments of the disclosure, various features are grouped together in one or more embodiments for streamlining the disclosure. This is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims are hereby incorporated into the detailed description of embodiments, with each claim standing on its own as a separate embodiment. It is understood that the above description is intended to be illustrative, and not restrictive. It is intended to cover all alternatives, modifications and equivalents as may be included within the scope of the disclosure as defined in the appended claims. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

As used in this disclosure, the term "circuit" is broadly meant to refer to hardware, software, and a combination of hardware and software. That is, a particular function may be implemented in specialized circuits, in software executing on general processor circuits, and/or a combination of specialized circuits, generalized circuits, and software.

The abstract is provided to comply with 37 C.F.R. 1.72(b) to allow a reader to quickly ascertain the nature and gist of the technical disclosure. The Abstract is submitted with the understanding that it will not be used to interpret or limit the scope or meaning of the claims.

The invention claimed is:

1. A processor-readable medium, comprising instructions that, when performed by the processor, cause the processor to:
   obtain information indicative of an acoustic signal from an implantable acoustic sensor;
   identify a first heart sound feature in the information indicative of the acoustic signal;
   obtain information indicative of a cardiac impedance from an implantable cardiac impedance sensor;
   transform the information indicative of the cardiac impedance to obtain transformed cardiac impedance information;
   identify a first cardiac impedance feature in the transformed cardiac impedance information;
   determine a first interval between the identified first heart sound feature in the information indicative of the acoustic signal and the identified first cardiac impedance feature in the transformed cardiac impedance information; and
   determine a heart failure decompensation status using information about the determined first interval.

2. The processor-readable medium of claim 1, wherein the first interval corresponds to a left ventricular ejection time (LVET), and wherein the instructions include instructions that, when performed by the processor, cause the processor to:
   determine a second interval corresponding to a pre-ejection period (PEP);
   determine a relative indication of information between the PEP and the LVET; and
   determine the heart failure decompensation status using the relative indication of information.

3. The processor-readable medium of claim 2, wherein the instructions to determine the relative indication of information include instructions to determine a ratio of the PEP to the LVET.

4. The processor-readable medium of claim 3, comprising instructions that, when performed by the processor, cause the processor to:
   determine respective instances of the ratio of the PEP to the LVET corresponding to respective cardiac cycles;
   identify a trend in the determined respective instances of the ratio of the PEP to the LVET; and determine a heart failure decompensation status using information about the identified trend.

5. The processor-readable medium of claim 4, wherein the identified trend includes identified information indicative of an increasing ratio of the PEP to the LVET.

6. The processor-readable medium of claim 2, comprising instructions that, when performed by the processor, cause the processor to:
obtain information indicative of cardiac electrical activity from an implantable cardiac electrical activity sensing circuit;
identify a cardiac electrical activity feature in the information indicative of the cardiac electrical activity; and
identify a second feature heart sound feature in the information indicative of the acoustic signal;
wherein the instructions that, when performed by the processor, cause the processor to determine the second interval between the identified cardiac electrical activity feature and the second heart sound feature.

7. The processor-readable medium of claim 1, comprising instructions that, when performed by the processor, cause the processor to:
determine respective instances of the first interval corresponding to respective cardiac cycles; and
identify a trend in the determined respective instances of the first interval;
wherein the instructions to determine the heart failure decompensation status using information about the determined first interval include instructions to determine the heart failure decompensation status using information about the identified trend.

8. The process-readable medium of claim 7, wherein the first interval corresponds to a left ventricular ejection time (LVET); and
wherein the identified trend includes identified information indicative of a decreasing LVET over multiple cardiac cycles.

9. The processor-readable medium of claim 1, wherein the instructions to transform the cardiac impedance information include instructions to obtain information indicative of respective slopes between respective points in the information indicative of the cardiac impedance.

10. The processor-readable medium of claim 1, wherein the instructions to transform the cardiac impedance information include instructions to obtain information indicative of a derivative of the information indicative of the cardiac impedance.

11. An implantable medical device comprising:
an acoustic sensor configured to provide information indicative of an acoustic signal obtained using the acoustic sensor;
a cardiac impedance sensing circuit configured to provide information indicative of a cardiac impedance obtained using the cardiac impedance sensing circuit;
a transform circuit coupled to the cardiac impedance circuit and configured to receive the information indicative of the cardiac impedance and configured to provide transformed cardiac impedance information; and
a processor circuit communicatively coupled to the to acoustic sensor and to the transform circuit, the processor circuit configured to:
receive the information indicative of the acoustic signal;
identify a first heart sound feature in the information indicative of the acoustic signal;
receive the transformed cardiac impedance information;
identify a first cardiac impedance feature in the transformed cardiac impedance information;
determine a first interval between the identified first heart sound feature in the information indicative of the acoustic signal and the identified first cardiac impedance feature in the transformed cardiac impedance information, the first interval corresponding to a left ventricular ejection time (LVET);
determine a second interval corresponding to a pre-ejection period (PEP);
determine a relative indication of information between the PEP and the LVET; and
determine a heart failure decompensation status using information about the relative indication of information.

12. A system, comprising:
an implantable medical device comprising:
an acoustic sensor configured to provide information indicative of an acoustic signal obtained using the acoustic sensor;
a cardiac impedance sensing circuit configured to provide information indicative of a cardiac impedance obtained using the cardiac impedance sensing circuit; and
a transform circuit coupled to the cardiac impedance circuit and configured to receive the information indicative of the cardiac impedance and configured to provide transformed cardiac impedance information; and
a processor circuit communicatively coupled to the to acoustic sensor and to the transform circuit, the processor circuit configured to:
receive the information indicative of the acoustic signal;
identify a first heart sound feature in the information indicative of the acoustic signal;
receive the transformed cardiac impedance information;
identify a first cardiac impedance feature in the transformed cardiac impedance information;
determine a first interval between the identified first heart sound feature in the information indicative of the acoustic signal and the identified first cardiac impedance feature in the transferred cardiac impedance information; and
determine a heart failure decompensation status using information about the determined first interval.

13. The system of claim 12, wherein the first interval corresponds to a left ventricular ejection time (LVET), and wherein the processor circuit is configured to:
determine a second interval corresponding to a pre-ejection period (PEP); and
determine a relative indication of information between the PEP and the LVET; and
determine the heart failure decompensation status using the relative indication of information.

14. The system of claim 13, wherein the processor circuit is configured to determine the relative indication of information including determining a ratio of the PEP to the LVET.

15. The system of claim 14, wherein the processor circuit is configured to:
determine respective instances of the ratio of the PEP to the LVET corresponding to respective cardiac cycles;
identify a trend in the determined respective instances of the ratio of the PEP to the LVET; and
determine a heart failure decompensation status using information about the identified trend.

16. The system of claim 15, wherein the identified trend includes identified information indicative of an increasing ratio of the PEP to the LVET.

17. The system of claim 13, wherein the processor circuit is configured:
   obtain information indicative of cardiac electrical activity from an implantable cardiac electrical activity sensing circuit;
   identify a cardiac electrical activity feature in the information indicative of the cardiac electrical activity;
   identify a second feature heart sound feature in the information indicative of the acoustic signal; and
   determine the second interval between the identified cardiac electrical activity feature and the second heart sound feature.

18. The system of claim 12, wherein the processor circuit is configured to:
   determine respective instances of the first interval corresponding to respective cardiac cycles;
   identify a trend in the determined respective instances of the first interval corresponding to respective cardiac cycles; and
   determine the heart failure decompensation status using information about the identified trend.

19. The system of claim 18, wherein the first interval corresponds to a left ventricular ejection time (LVET); and
   wherein the identified trend includes identified information indicative of a decreasing LVET over multiple cardiac cycles.

20. The system of claim 12, further comprising an adjunct device; and
   wherein the processor circuit is included as a portion of the adjunct device.

* * * * *